United States Patent [19]

Musser et al.

[11] Patent Number: 4,681,940

[45] Date of Patent: Jul. 21, 1987

[54] 5-[3-[[2-QUINOLYL]METHOXY]PHENYL]-1,3-OXAZOLES

[75] Inventors: John H. Musser, Malvern; Reinhold H. W. Bender, Valley Forge, both of Pa.

[73] Assignee: American Home Products Corporation, New York, N.Y.

[21] Appl. No.: 799,673

[22] Filed: Nov. 19, 1985

[51] Int. Cl.$^4$ ................. C07D 417/12; C07D 413/12; C07D 413/14
[52] U.S. Cl. ................................... 546/174; 546/176; 548/232; 548/325
[58] Field of Search .......................... 546/174, 176

[56] References Cited

FOREIGN PATENT DOCUMENTS 0110405  6/1984  European Pat. Off. .

OTHER PUBLICATIONS

Musser et al., Synthetic Communications, 14, 947–53 (1984).

Primary Examiner—Glennon H. Hollrah
Assistant Examiner—D. B. Springer
Attorney, Agent, or Firm—George Tarnowski

[57] ABSTRACT

There are disclosed compounds of the formula

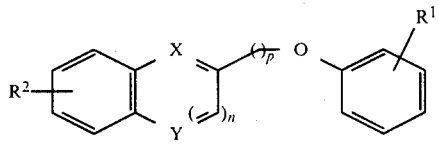

wherein
X is N or $CR^2$
Y is O, S, $NR^2$, $CHR^2$ or $C(R^2)_2$ when n=0, or N or $CR^2$ when n=1;
p is 0–3;
$R^1$ is

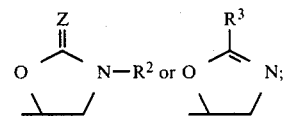

$R^2$ is hydrogen or lower alkyl;
$R^3$ is hydrogen, lower alkyl, phenyl, thienyl, furyl, pyridyl,

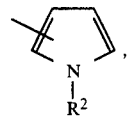

—$C(R^4)_3$ or —$(CH_2)_pCOOR^2$;
$R^4$ is halo;
Z is O or S;

and the pharmaceutically acceptable salts thereof, and their use in the treatment of luekotriene-mediated naso-bronchial obstructive airpassageway conditions, such as allergic rhinitis, allergic bronchial asthma and the like, in psoriasis, ulcerative colitis, rheumatoid arthritis as well as in other immediate hypersensitivity reactions.

7 Claims, No Drawings

5-[3-[[2-QUINOLYL]METHOXY]PHENYL]-1,3-OXAZOLES

This invention relates to novel heterocyclic compounds possessing 5-lipoxygenase inhibitory and leukotriene antagonist activity, which are useful as anti-inflammatory and antiallergic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$, $D_4$ and $E_4$. The substance denominated slow-reacting substance of anaphylaxis (SRS-A) has been shown to consist of a mixture of sulfidopeptide leukotrienes, $C_4$, $D_4$ and $E_4$ [see Bach et al., *J. Immun.* 215, 115–118 (1980); *Biochem. Biophys. Res. Commun.* 93, 1121–1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980) and Piper, *Int. Arch. Appl. Immunol.*, 76, suppl. 1, 43 (1985)] are potent vasodilators in skin [see Bisgaard et al, *Prostaglandins*, 23, 797 (1982)], and produce a weal and flare response [Camp et al., *Br. J. Pharmacol,*, 80, 497 (1983)]. The nonpeptide leukotriene, $LTB_4$, is a powerful chemotactic factor for leukocytes [see A. W. Ford-Hutchinson, *J. Roy. Soc. Med.*, 74, 831–833 (1981)], which stimulates cell accumulation and affects vascular smooth muscle [see Bray, *Br. Med. Bull.*, 39, 249 (1983)]. The activity of leukotrienes as mediators of inflammation and hypersensitivity is extensively reviewed in Bailey and Casey, *Ann. Reports Med. Chem.*, 17, 203–217 (1982).

The biological activity of the leukotrienes, and of lipoxygenase as the enzyme leading to the metabolism of AA to leukotrienes, indicates that a rational approach to drug therapy to prevent, remove or ameliorate the symptoms of allergies, anaphylaxis, asthma and inflammation must focus on either blocking the release of mediators of these conditions or to antagonize their effects. Thus, compounds which inhibit the biological effects of the leukotrienes and/or which control the biosynthesis of these substances, as by inhibiting lipoxygenase, are considered to be of value in treating such conditions as allergic bronchial asthma, allergic rhinitis, psoriasis, ulcerative colitis, rheumatoid arthritis, as well as in other immediate hypersensitivity reactions.

The invention provides novel compounds of the formula

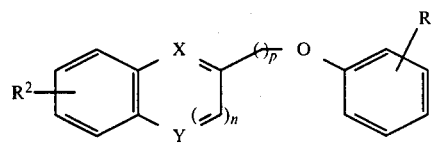

wherein
X is N or $CR^2$
Y is O, S, $NR^2$, $CHR^2$ or $C(R^2)_2$ when n=0, or N or $CR^2$ when n=1;
p is 0–3;
$R^1$ is

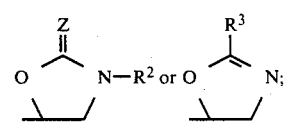

$R^2$ is hydrogen or lower alkyl;
$R^3$ is hydrogen, lower alkyl, phenyl, thienyl, furyl, pyridyl,

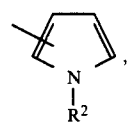

—$C(R^4)_3$ or —$(CH_2)_pCOOR^2$;
$R^4$ is is halo;
Z is O or S;
and the pharmaceutically acceptable salts thereof.

The term "lower alkyl" refers to moieties having 1 to 6 carbon atoms in the carbon chain. The term "halo" refers to fluoro, chloro and bromo.

The compounds of the invention in which $R^1$ is

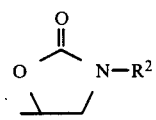

can be prepared by the reaction of an appropriate phenylephrine derivative with an appropriate benzo-fused heterocyclic derivative as follows, exemplified with an R-phenylephrine derivative:

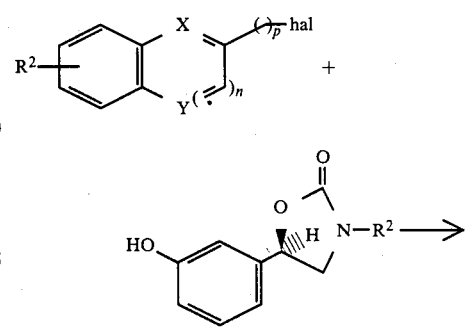

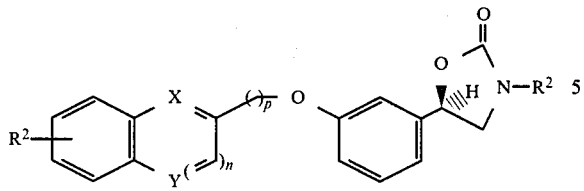

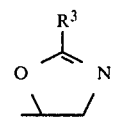

can be prepared in the same manner as when R¹ is

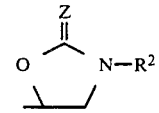

where X, Y, R¹, n and p are as defined hereinbefore and hal refers to a halo radical, for example, chloro, bromo or iodo. The reaction is carried out in the presence of a base, such as cesium carbonate, in an organic solvent, for instance acetone, under reflux conditions.

using an appropriate starting phenylephrine derivative.

The starting phenylephrine derivatives in which $Z=O$ can be prepared as follows:

If an S-phenylephrine derivative is employed as the starting material, the corresponding enantiomeric final product is obtained:

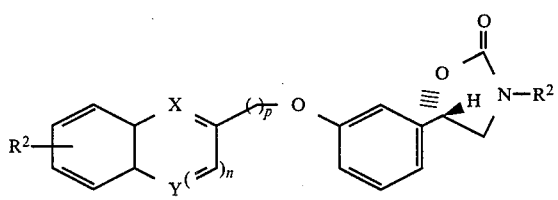

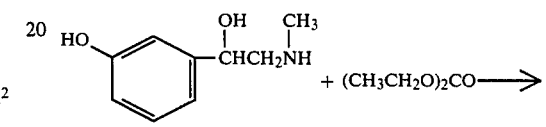

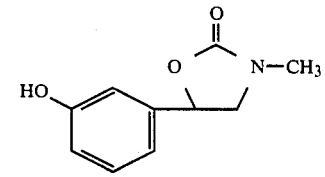

Compounds in which Z in $R_1$ is S can be prepared by the following alternative reaction scheme:

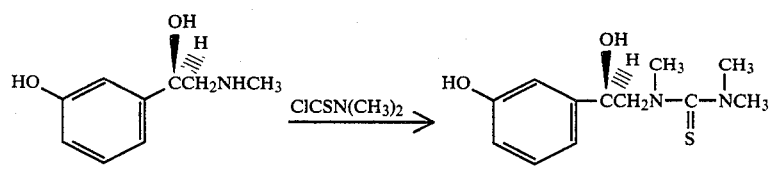

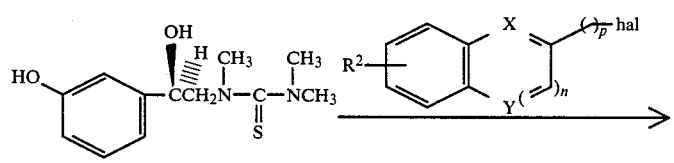

In this reaction scheme, the preparation of the phenylephrine intermediate is carried out in the presence of triethylamine in an organic solvent, for instance, tetrahydrofuran. The reaction of the phenylephrine intermediate with the appropriate benzo-fused heterocyclic derivative is carried out in the presence of a base, such as cesium carbonate, in an organic solvent, for instance acetone, under reflux conditions.

The compound of the invention in which R¹ is

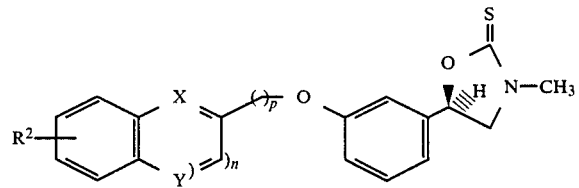

This reaction is carried out under reflux conditions in the presence of a base, such as potassium carbonate. The starting phenylephrine derivatives in which R¹ is

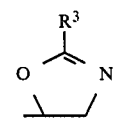

can be prepared according to the following exemplifying schemes, wherein the starting compound is (±) norphenylephrine

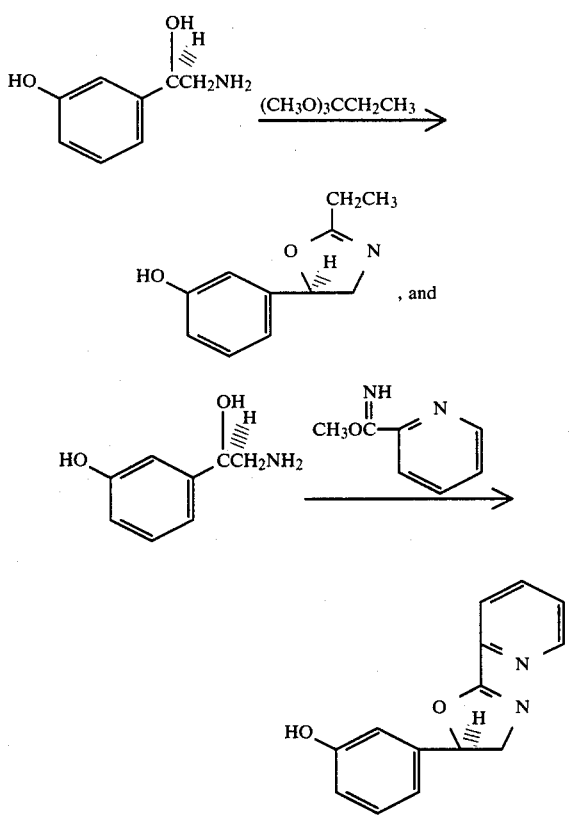

The above reactions are carried out at elevated temperature, neat or in an organic solvent, such as tetrahydrofuran, in the presence of triethylamine.

The benzo-fused heterocyclic compounds used in the above reactions are either commercially available or can be prepared by methods conventional in the art. Thus, for example, such intermediates as 1-methyl-2-chloromethylbenzimidazole, 2-chloromethylbenzthiazole and 2-chloromethylbenzoxazole can be prepared by the following reaction scheme

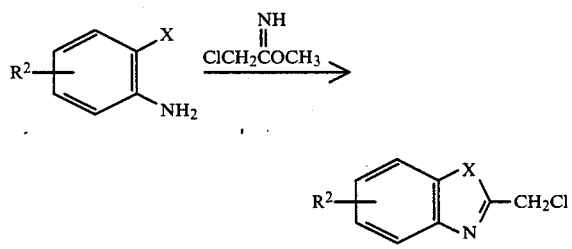

wherein X is O, S or NCH₃. The reaction is preferably carried out at a controlled low temperature in an organic solvent, such as methylene chloride.

By virtue of the chirality in the phenylephrine molecule, the final products also possess chirality. Since the absolute configuration is known, the starting phenylephrine compounds and final product enantiomers can be differentiated by the prefixes R and S, as assigned by the accepted sequence rule procedures. Accordingly, the present invention embraces the R, S and RS forms of phenylephrine, norphenylephrine, of their derivatives, and of the final products.

Compounds of the invention which contain a basic nitrogen are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic and the like.

The compounds of the invention, by virtue of their ability to inhibit the activity of lipoxygenase enzyme and by their ability to antagonize the effects of LTD₄ and LTC₄, are useful for the inhibition of symptoms induced by these leukotrienes. Accordingly, the compounds are indicated in the prevention and treatment of those disease states in which the leukotrienes are causative factors, for example allergic rhinitis, allergic bronchial asthma and other leukotriene mediated naso-bronchial obstructive air-passageway conditions, psoriasis, ulcerative colitis, rheumatoid arthritis, as well as in other immediate hypersensitivity reactions, such as allergic conjunctivitis. The compounds are especially valuable in the prevention and treatment of allergic bronchial asthma.

When the compounds of the invention are employed in the treatment of allergic airways disorders and/or as antiinflammatory agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase inhibitory and leukotriene antagonist effects of the compounds of the invention may be demonstrated by standard pharmacological procedures, which are described more fully in the examples given hereinafter.

These procedures illustrate the ability of the compounds to inhibit the polymorphonuclear leukocyte synthesis of the lipoxygenase product 5-HETE, the in vivo ability of the compounds to antagonize LTD₄- induced bronchospasm mediated by exogenously administered leukotrienes and measure the in vivo activity of the compounds as lipoxygenase inhibitors and leukotriene antagonists of endogenous mediators of bronchospasm.

The following examples show the preparation and pharmacological testing of compounds within the invention.

EXAMPLE 1

5-[3-[(2-Quinolinyl)methoxy]phenyl]-3-methyl-2-oxazolidone

A. 5-(3-Hydroxyphenyl)-3-methyl-2-oxazolidone

A mixture of R-phenylephrine hydrochloride (20.0 g, 0.098 mol), potassium carbonate (13.6 g, 0.098 mol) and diethyl carbonate (200 ml) is refluxed for 4 hours. During the reaction, ethanol is removed by distillation. The mixture is allowed to stand at room temperature overnight. Excess diethyl carbonate is decanted and the remaining solid is partially dissolved in acetone. The acetone extract is filtered through celite and silica gel and the solvent is removed in vacuo to give 9.6 (51% yield) of product as an oil

B. 5-[3-[(2-Quinolinyl)methoxy]phenyl]-3-methyl-2-oxazolidone

A mixture of 5-(3-hydroxyphenyl)-3-methyl-2-oxazolidone (9.6 g, 0.05 mol), 2-(chloromethyl)quinoline hydrochloride (10.6 g, 0.05 mol), cesium carbonate (16.0 g, 0.05 mol) and acetone (300 ml) is refluxed for 2 days. The reaction is filtered through celite and silica gel and the solvent is removed in vacuo giving an oil. The oil is purified by HPLC using a 9:1 mixture of chloroform/acetone as an eluent. Crystallization of the oil from fractions 6-9 gives 10.5 g (63% yield) of product, m.p. 75°-77° C., $[\alpha]^{26} = -11.54$ (1% in CHCl$_3$).

Following the above procedures and using S-phenylephrine hydrochloride, the S-enantiomer of the named compound is prepared, m.p. 74°-77° C., $[\alpha]^{26} = +12.15.$ (1% in CHCl$_3$).

EXAMPLE 2

5-[3-[(2-Quinolinyl)methoxy]phenyl]-3-methyl-2-thiaoxazolidone

A. 1-(3-Hydroxyphenyl)-2-(N-methyl-N-dimethylthiocarbamoyl)amino ethanol

To a suspension of phenylephrine hydrochloride (20.4 g, 0.1 mol) in tetrahydrofuran (500 ml) with triethylamine (27.8 ml) is slowly added dimethylthiocarbamoyl chloride (12.4 g, 0.1 mol). The reaction is stirred for 2 hours at room temperature. The mixture is filtered through celite and silica gel and the solvent is removed in vacuo giving an oil. The oil is purified by HPLC using hexane/methylene chloride gradient elution. Crystallization of the oil from fraction 6 gives 11.9 g (47% yield) of product, m.p. 95°-79° C.

B. 5-[3-[(2-Quinolinyl)methoxy]phenyl]-3-methyl-2-thiaoxazolidone

A mixture of 1-(3-hydroxyphenyl)-2-(N-methyl-N-dimethylthio-carbamoyl)amino ethanol (5.08 g, 0.02 mol), 2-(chloromethyl)quinoline hydrochloride (4.28 g, 0.02 mol), cesium carbonate (6.5 g, 0.02 mol) and acetone (400 mol) is refluxed overnight. The mixture is filtered through celite and silica gel and the solvent is removed in vacuo giving an oil. The oil is purified by HPLC using 7:3 ratio of hexane/ethyl acetate as an eluent. Crystallization of the oil from fraction 13 gives 280 mg (3.5% yield) of product, m.p. 122°-124° C.

EXAMPLE 3

5-[3-[(2-Benzthiazolyl)]methoxy]phenyl-3-methyl-2-oxazolidone

A. 2-Chloromethylbenzthiazole

To a solution of 2-aminothiophenol (8.3 g) in methylene chloride at 0° C. is added methyl chloroacetimidate hydrochloride[1] (8.6 g). The reaction is allowed to warm to room temperature while stirring overnight. The mixture is washed with water (3X); dried over MgSO$_4$ and concentrated to an oil. The oil is distilled (120°-135° C. at 0.5 mm Hg) to give 7.8 g (71% yield) of product.

[1]Prepared according to the procedure described in Roger et al., Chem. Rev., 61, 179 (1961).

5-[3-[(2-Benzthiazolyl)]methoxy]phenyl]-3-methyl-2-oxazolidone

Using the compound prepared in A. above, the title compound is prepared using the procedure Example 1B; m.p. 146°-147° C.

EXAMPLE 4

5-[3-[(1-Methyl-2-benzimidazoyl)]methoxy]phenyl-3-methyl-2-oxazolidone

Following the procedure of Example 3, and using the appropriate starting materials and reagents, the title compound is prepared, m.p. 120°-122° C.

EXAMPLE 5

2-Ethyl-4,5-dihydro-5-[3-[(2-quinolinyl)-methoxy]phenyl]-3-oxazole

A. 2-Ethyl-4,5-dihydro-5-(3-hydroxyphenyl)-1,3-oxazole

A mixture of (±)-norphenylephrine hydrochloride (10 g, 0.05 mol), triethylamine (5 g, 0.05 mol) and triethylorthoformate (100 ml) is heated for 2 hours at 90° C. The mixture is then concentrated to dryness and the residue is dissolved in ethyl acetate and dilute aqueous sodium bicarbonate solution. The ethyl acetate layer is washed with dilute aqueous sodium bicarbonate solution and dilute aqueous sodium chloride solution, dried over anhydrous magnesium sulfate, and concentrated to dryness to obtain 6 g of crude material, m.p. <84°. This material is dissolved in hot ethyl acetate, the solution is filtered, diluted with hexane and allowed to cool. The resulting crystals (3.5 g) are filtered off, washed with ethyl acetate/hexane, and dried in vacuo, m.p. 145°-6° C.

B. 2-Ethyl-4,5-dihydro-5-[3-[(2-quinolinyl)methoxy]phenyl]-1,3-oxazole

A solution of 2-ethyl-4,5-dihydro-5-(3-hydroxyphenyl)-1,3-oxazole (3.5 g, 0.018 mol) and 2-(chloromethyl)quinoline (3.5 g, 0.02 mol) in acetone (300 ml) is heated at reflux for 48 hours in the presence of cesium carbonate (3.3 g, 0.01 mol). After cooling, the insoluble material is filtered off and washed with acetone. The acetone solution and wash are concentrated to dryness and the residue is dissolved in ethyl acetate. The solution is washed twice with dilute aqueous sodium bicarbonate solution, dried over anhydrous magnesium sulfate and concentrated to dryness to obtain 6.8 g of crude material. This material is chromatographed on a Waters silica Prep Pak column with methylene chloride/methanol 99/1 (v/v) as mobile phase to obtain 4 g of purified material. This oil is dissolved in ethyl acetate, the solution is stirred with charcoal, and filtered on celite. The solution is concentrated to dryness and the residual oil is dried in vacuo.

EXAMPLE 6

4,5-Dihydro-5-[3-[(2-quinolinyl)methoxy]phenyl]-2-(2-pyridyl)-1,3-oxazole

A.

4,5-Dihydro-5-(3-hydroxyphenyl)-2-(2-pyridyl)-1,3-oxazole

A mixture of (±) norphenylephrine hydrochloride (10 g, 0.05 mol) and methyl iminopicolinate (8 g, 0.059 mol) in tetrahydrofuran (300 ml) is heated to reflux for 16 hours. The mixture is dissolved in ethyl acetate and water. The aqueous layer is extracted twice with ethyl acetate. The combined ethyl acetate solutions are washed twice with dilute aqueous sodium chloride solution, dried over anhydrous magnesium sulfate and concentrated to dryness to obtain a partially crystalline material. This material is triturated with ether to obtain crystals. These crystals are dissolved in hot acetonitrile and the hot solution is filtered and allowed to cool. The crystals (4 g) are filtered off, washed with acetonitrile and dried in vacuo, m.p. 139°–141° C.

B.

4,5-Dihydro-5-[3-[(2-quinolinyl)methoxy]phenyl]-2-(2-pyridyl)-1,3-oxazole

A solution of 4,5-dihydro-5-(3-hydroxyphenyl)-2-(2-pyridyl)-1,3-oxazole (7.3 g, 0.03 mol) and 2-(chloromethyl)quinoline (5.4 g, 0.03 mol) in dimethylformamide (200 ml) is heated to 90° for 16 hours in the presence of sodium methoxide (1.6 g, 0.03 mol). The mixture is dissolved in ethyl acetate and water. The aqueous layer is extracted twice with ethyl acetate. The combined ethyl acetate solutions are washed twice with dilute aqueous sodium chloride solution, dried over anhydrous magnesium sulfate and concentrated to obtain an oil. This material is chromatographed on a Water Prep Pak 500 silica column with methylene chloride/methanol 99/1 (v/v) as mobile phase to obtain 2.5 g of purified material as a viscous oil.

EXAMPLE 7

4,5-Dihydro-5-[3-[(2-quinolinyl)methoxy]phenyl]-2-(2-thienyl)-1,3-oxazole

A.

4,5-Dihydro-5-(3-hydroxyphenyl)-2-(2-thienyl)-1,3-oxazole

A mixture of (±) norphenylephrine hydrochloride (10 g, 0.05 mol), ethyl thiophene-2-imidate hydrochloride (10 g, 0.05 mol) and triethylamine (5 g, 0.05 mol) in tetrahydrofuran (300 ml) is heated to reflux for 8 hours. The mixture is dissolved in ethyl acetate and water. The aqueous layer is extracted twice with ethyl acetate. The combined ethyl acetate solutions are washed twice with dilute aqueous sodium chloride solution, dried over anhydrous magnesium sulfate and concentrated to dryness to obtain a viscous, partly crystalline material (10 g). This material is triturated with ether to obtain crystals (5 g) of m.p. 150°. These crystals are dissolved in hot acetonitrile and the solution is filtered and allowed to cool. The crystals (3.4 g) are filtered off, washed with acetonitrile and dried in vacuo; m.p. 156°–158° C.

B.

4,5-Dihydro-5-[3-[(2-quinolinyl)methoxyphenyl]-2-(2-thienyl)-1,3-oxazole

A solution of 4,5-dihydro-5-(3-hydroxyphenyl)2-(2-thienyl)-1,3-oxazole (8.3 g, 0.034 mol) and 2-(chloromethyl)quinoline (6 g, 0.034 mol) in acetone (300 ml) is heated at reflux for 48 hours in the presence of cesium carbonate (5.6 g, 0.017 mol). After cooling, the insoluble material is filtered off and washed with acetone. The acetone solution and wash are concentrated to dryness, and the residue is dissolved in ethyl acetate. The solution is washed twice with dilute aqueous sodium chloride solution, dried over anhydrous magnesium sulfate and concentrated to obtain 13.8 g of crude material. This material is chromatographed on two Waters Prep Pak 500 silica columns with methylene chloride/isopropanol 98/2 (v/v) as mobile phase to obtain 5 g of purified material. This material is dissolved in hot ethyl acetate and the solution is diluted with hexane. The crystals (4.1 g) are filtered off, washed with ethyl acetate/hexane and dried in vacuo; m.p. 108°–110° C.

EXAMPLE 8

2-Ethoxycarbonylmethyl-4,5-dihydro-5-[3-[(2-quinolinyl)methoxy]phenyl]-1,3-oxazole Following the procedure of Example 7A. and using (±) norphenylephrine and ethyl ethoxycarbonyl acetimidate hydrochloride, there is obtained 2-ethoxycarbonylmethyl-4,5-dihydro-5-(3-hydroxyphenyl)-1,3-oxazole. The latter is reacted with 2-(chloromethyl)quinoline following the procedure of Example 1B, to obtain the title compound, m.p. 94°–95° C.

EXAMPLE 9

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. The assay of this Example measures the ability of the compounds of the invention to inhibit the synthesis of 5-HETE by rat glycogen elicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing $Ca^{++}$ and $Mg^{++}$ and 10 mM L-cysteine at a concentration of $2 \times 10^7$ cells/ml. To 1 ml portions of cell suspension, test drugs or vehicle are added and incubated at 37° C. for 10 minutes. Following this preincubation, the calcium ionophore (10 μM), A23187, is added together with 0.5 μCi [$^{14}$C] arachidonic acid and further incubated for 10 minutes. The reaction is stopped by the addition of ice cold water (3 ml) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5-HETE in the solvent system—hexane:ether:acetic acid (50:50:3). After chromatography, the areas associated with 5-HETE standard are identified by autoradiography, cut out and quantitated by liquid scintillation.

The compounds of this invention are tested in this assay at a level of 50 μm, unless otherwise noted. The results are summarized in Table 1, where those compounds having an inhibition of >50% are designated by a "+". Some results are expressed as an $IC_{50}$ value.

TABLE 1

| Compound of Example Number | >50% Inhibitory at 50 μm | ($IC_{50}$) μm |
|---|---|---|
| 1 | + | 19.6 |
| 2 | + | |

The results show that compounds of this invention have significant activity in inhibiting the synthesis of the arachidonic acid lipoxygenase oxidation product 5-HETE.

EXAMPLE 10

The assay of this Example measures the in vivo ability of the compounds of the invention to inhibit the bronchospasm induced in guinea pigs by the exogenously administered leukotrienes $C_4$ and/or $D_4$.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes as described infra. The animals are then pretreated with succinylcholine (2 mg/kg i.v.) and indomethacin (10 mg/kg i.v. in trizma 8.3 buffer, 9 minutes prior to leukotriene challenge). Submaximal bronchoconstrictor responses are established in control animals by varying the dose-levels of leukotriene. Intravenous dose-levels for $LTC_4$ range from 0.4 to 0.6 μg/kg and for $LTD_4$ the range is from 0.3 to 0.5 μg/kg. The aerosol bronchoprovocation dose for $LTC_4$ is generated from 1.6 μM solution and for $LTD_4$ from a 2.0 μM solution.

Test drugs (dissolved in a solvent such as propylene glycol, polyethylene glycol 400 or saline) are administered either intraduodenally, by aerosol or intragastrically at 2 or 10 minutes before induction of bronchospasm by administration of either $LTC_4$ or $LTD_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Student's t-test for unpaired data is used to determine statistical significance (p<0.05). $IC_{50}$ values can also be determined by inverse prediction from linear regression lines through points between 10 and 90% inhibition.

The results for compounds of the invention are as follows:

| Compound administered at 10 minutes before induction of bronchospasm | | | |
|---|---|---|---|
| Compound of Example Number | Dose mg/kg | % Inhibition | $IC_{50}$ mg/kg |
| 1 (as HCL salt) | 50* | 65 | |
|  | 50** | 46 | |
| 1 (as free base, R-enantiomer) | 50* | 91 | 8.6 |
|  | 50** | 65 | |
| 1 (as free base, S-enantiomer) | 50* | 99 | |
| 4 | 50* | 65 | |
| 5 | 25* | 77 | |
| 6 | 25* | 96 | |
| 7 | 50* | 41 | |
| 8 | 25* | 72 | |

\* = intraduodenally administered
\*\* = intragastrically administered

The results show that compounds of the invention have significant in vivo activity against $LTD_4$ induced bronchoconstriction.

EXAMPLE 11

The assay of this Example measures the in vivo ability of the compounds of the invention to inhibit the bronchospasm induced in guinea pigs by endogenous mediators of the bronchoconstriction.

The assay is carried out as follows:

Male Hartley strain guinea pigs weighing 250–350 g are sensitized to chicken ovalbumin (OA) (10 mg i.p.) on days 1 and 3 and used starting on day 26. The animals are anesthetized with pentobarbital sodium (50 mg/kg, i.p.), bilateral vagotomy is performed, and the jugular vein is cannulated for injection of drugs and the carotid artery for monitoring blood pressure. The trachea is cannulated for artificial ventilation by miniature Starling pump and for indirect measurement of respiratory volume changes as described, infra. Succinylcholine (2 mg/kg, i.v.) is administered to arrest spontaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs (dissolved in propylene glycol, polyethylene glycol or saline) are administered either intraduodenally or by aerosol at 2 or 10 minutes before antigen challenge. Anaphylactic bronchoconstriction is induced by administration by breaths of aerosolized OA (1%) or by intravenous administration of 0.1-0.3 mg/kg OA in saline. Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Students t-test for unpaired data is used to determine statistical significance. Dose response curves are generated and $ED_{50}$ doses are interpolated from the regression lines.

Results for compounds of the invention in this assay, using OA for induction of bronchospasm, are given below:

| Compound administered at 10 minutes before intraduodenally administered ovalbumin challenge | | |
|---|---|---|
| Compound of Example Number | Dose mg/kg (Intraduodenal) | % Inhibition of Max AUC |
| 1 (as free base) | 50 | 69 |

The results show that the compound tested has significant in vivo activity in inhibiting ovalbumin induced bronchospasm mediated by endogenous products of the lipoxygenase oxidation of arachidonic acid.

What is claimed is:

1. A compound having the formula

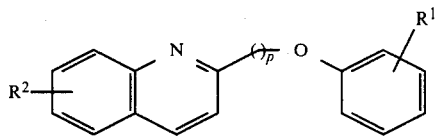

wherein
$R^1$ is

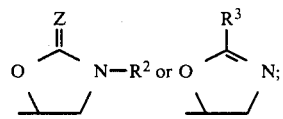

$R^2$ is hydrogen or lower alkyl;
$R^3$ is hydrogen, lower alkyl, phenyl, thienyl, furyl, pyridyl, $CF_3$, $-(CH_2)_pCOOR^2$ or

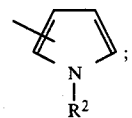

P is 0-3
Z is O or S;
and the pharmaceutically acceptable salts thereof.

2. The compound of claim 1, which is 5-[3-[(2-quinolinyl)methoxy]phenyl]-3-methyl-2-oxazolidone.

3. The compound of claim 1, which is 5-[3-[(2-quinolinyl)methoxy]phenyl]-3-methyl-2-thiaoxazolidone.

4. The compound of claim 1, which is 2-ethyl-4,5-dihydro-5-[3-[(2-quinolinyl)methoxy]phenyl]-3-oxazole.

5. The compound of claim 1, which is 4,5-dihydro-5-[3-[(2-quinolinyl)methoxy]phenyl]-2-(2-pyridyl)-1,3-oxazole.

6. The compound of claim 1, which is 4,5-dihydro-5-[3-[(2-quinolinyl)methoxy]phenyl]-2-(2-thienyl)-1,3-oxazole.

7. The compound of claim 1, which is 2-ethoxycarbonylmethyl-4,5-dihydro-5-[3-[(2-quinolinyl)methoxy]phenyl]-1,3-oxazole.

* * * * *